United States Patent

Richard

(10) Patent No.: US 9,474,518 B2
(45) Date of Patent: Oct. 25, 2016

(54) EXPANDING SEAL ANCHOR FOR SINGLE INCISION SURGERY

(71) Applicant: Covidien LP, Mansfield, MA (US)

(72) Inventor: Paul D. Richard, Shelton, CT (US)

(73) Assignee: Covidien LP, Mansfield, MA (US)

( * ) Notice: Subject to any disclaimer, the term of this patent is extended or adjusted under 35 U.S.C. 154(b) by 153 days.

(21) Appl. No.: 14/310,024

(22) Filed: Jun. 20, 2014

(65) Prior Publication Data

US 2014/0303669 A1    Oct. 9, 2014

Related U.S. Application Data

(63) Continuation of application No. 12/244,127, filed on Oct. 2, 2008, now Pat. No. 8,795,326.

(60) Provisional application No. 60/997,844, filed on Oct. 5, 2007.

(51) Int. Cl.
| | |
|---|---|
| *A61B 17/02* | (2006.01) |
| *A61B 17/34* | (2006.01) |
| *A61B 17/00* | (2006.01) |

(52) U.S. Cl.
CPC ....... *A61B 17/0293* (2013.01); *A61B 17/0057* (2013.01); *A61B 17/3423* (2013.01); *A61B 17/3439* (2013.01); *A61B 2017/349* (2013.01); *A61B 2017/3419* (2013.01); *A61B 2017/3429* (2013.01); *A61B 2017/3484* (2013.01); *A61B 2090/037* (2016.02)

(58) Field of Classification Search
CPC .......... A61B 17/0057; A61B 17/3423; A61B 17/0293; A61B 17/3431; A61M 25/02
See application file for complete search history.

(56) References Cited

U.S. PATENT DOCUMENTS

| | | |
|---|---|---|
| 67,545 A | 8/1867 | Hodgins et al. |
| 219,296 A | 9/1879 | Naylor, Jr. |
| 319,296 A | 6/1885 | Molesworth |

(Continued)

FOREIGN PATENT DOCUMENTS

| | | |
|---|---|---|
| DE | 3321621 A1 | 12/1984 |
| DE | 3713831 A1 | 12/1988 |

(Continued)

OTHER PUBLICATIONS

European Search Report for corresponding EP 08253232 date of mailing is Feb. 11, 2009 (3 pages).

(Continued)

*Primary Examiner* — Christian Sevilla (57) ABSTRACT

The present disclosure relates to a surgical anchoring apparatus for use during a minimally invasive surgical procedure. The surgical anchoring apparatus includes a body member and a dilator element at least partially positionable therein. The body member includes a grip segment adapted for manual engagement by a user and an expandable section having a plurality of expandable segments and a plurality of cam surfaces. The grip segment resiliently transitions between a first or normal state and a second state in which the grip segment is at least partially inverted. The expandable section's cam surfaces are configured to engage a distal end of the dilator element upon its insertion such that the expandable section may transition from an initial condition to an expanded condition in which the body member is secured or anchored within an incision in tissue.

16 Claims, 4 Drawing Sheets

(56) References Cited

U.S. PATENT DOCUMENTS

| | | |
|---|---|---|
| 668,879 A | 2/1901 | Miller |
| 702,789 A | 6/1902 | Gibson |
| 1,213,001 A | 1/1917 | Phillips |
| 1,248,492 A | 12/1917 | Hill |
| 2,548,602 A | 4/1948 | Greenburg |
| 2,566,499 A | 9/1951 | Richter |
| 3,308,819 A | 3/1967 | Arp |
| 3,509,883 A | 5/1970 | Dibelius |
| 3,545,443 A | 12/1970 | Ansari et al. |
| 3,653,388 A | 4/1972 | Tenckhoff |
| 3,742,958 A | 7/1973 | Rundles |
| 3,750,667 A | 8/1973 | Pshenichny et al. |
| 3,788,318 A | 1/1974 | Kim et al. |
| 3,789,852 A | 2/1974 | Kim et al. |
| 3,811,449 A | 5/1974 | Gravlee et al. |
| 3,856,021 A | 12/1974 | McIntosh |
| 3,877,427 A | 4/1975 | Alexeev et al. |
| 3,893,454 A | 7/1975 | Hagelin |
| 3,902,492 A | 9/1975 | Greenhalgh |
| 3,952,742 A | 4/1976 | Taylor |
| 3,968,800 A | 7/1976 | Vilasi |
| 4,018,230 A | 4/1977 | Ochiai et al. |
| 4,141,364 A | 2/1979 | Schultze |
| 4,183,102 A | 1/1980 | Guiset et al. |
| 4,204,541 A | 5/1980 | Kapitanov |
| 4,320,762 A | 3/1982 | Bentov |
| 4,402,685 A | 9/1983 | Buhler et al. |
| 4,411,655 A | 10/1983 | Schreck |
| 4,447,237 A | 5/1984 | Frisch et al. |
| 4,461,281 A | 7/1984 | Carson |
| 4,479,497 A | 10/1984 | Fogarty et al. |
| 4,493,701 A | 1/1985 | Bootman et al. |
| RE31,855 E | 3/1985 | Osborne |
| 4,504,268 A | 3/1985 | Herlitze |
| 4,578,061 A | 3/1986 | Lemelson |
| 4,581,019 A | 4/1986 | Curelaru et al. |
| 4,581,025 A | 4/1986 | Timmermans |
| 4,585,437 A | 4/1986 | Simms |
| 4,589,868 A | 5/1986 | Dretler |
| 4,601,713 A | 7/1986 | Fuqua |
| 4,610,668 A | 9/1986 | Fleig |
| 4,630,609 A | 12/1986 | Chin |
| 4,650,466 A | 3/1987 | Luther |
| 4,706,670 A | 11/1987 | Andersen et al. |
| 4,716,901 A | 1/1988 | Jackson et al. |
| 4,738,666 A | 4/1988 | Fuqua |
| 4,739,762 A | 4/1988 | Palmaz |
| 4,753,636 A | 6/1988 | Free |
| 4,772,266 A | 9/1988 | Groshong |
| 4,798,193 A | 1/1989 | Giesy et al. |
| 4,817,587 A | 4/1989 | Janese |
| 4,846,791 A | 7/1989 | Hattler et al. |
| 4,846,812 A | 7/1989 | Walker et al. |
| 4,865,593 A | 9/1989 | Ogawa et al. |
| 4,869,717 A | 9/1989 | Adair |
| 4,888,000 A | 12/1989 | McQuilkin et al. |
| 4,896,669 A | 1/1990 | Bhate et al. |
| 4,899,729 A | 2/1990 | Gill et al. |
| 4,921,479 A | 5/1990 | Grayzel |
| 4,941,874 A | 7/1990 | Sandow et al. |
| 4,954,126 A | 9/1990 | Wallsten |
| 4,955,895 A | 9/1990 | Sugiyama et al. |
| 4,972,827 A | 11/1990 | Kishi et al. |
| 4,986,830 A | 1/1991 | Owens et al. |
| 4,996,583 A | 2/1991 | Hatada |
| 4,998,539 A | 3/1991 | Delsanti |
| 5,002,557 A | 3/1991 | Hasson |
| 5,002,577 A | 3/1991 | Bolesky et al. |
| 5,009,643 A | 4/1991 | Reich et al. |
| 5,021,241 A | 6/1991 | Yamahira et al. |
| D318,733 S | 7/1991 | Wyzgala |
| 5,041,093 A | 8/1991 | Chu |
| 5,045,056 A | 9/1991 | Behl |
| 5,069,674 A | 12/1991 | Fearnot et al. |
| 5,100,388 A | 3/1992 | Behl et al. |
| 5,104,388 A | 4/1992 | Quackenbush |
| 5,112,304 A | 5/1992 | Barlow et al. |
| 5,116,318 A | 5/1992 | Hillstead |
| 5,122,122 A | 6/1992 | Allgood |
| 5,139,485 A | 8/1992 | Smith et al. |
| 5,139,511 A | 8/1992 | Gill et al. |
| 5,141,497 A | 8/1992 | Erskine |
| 5,147,316 A | 9/1992 | Castillenti |
| 5,158,545 A | 10/1992 | Trudell et al. |
| 5,176,128 A | 1/1993 | Andrese |
| 5,183,464 A | 2/1993 | Dubrul et al. |
| 5,183,465 A | 2/1993 | Xanthakos et al. |
| 5,188,602 A | 2/1993 | Nichols |
| 5,197,971 A | 3/1993 | Bonutti |
| 5,201,756 A | 4/1993 | Horzewski et al. |
| 5,207,647 A | 5/1993 | Phelps |
| 5,221,263 A | 6/1993 | Sinko et al. |
| 5,222,938 A | 6/1993 | Behl |
| 5,222,971 A | 6/1993 | Willard et al. |
| 5,226,899 A | 7/1993 | Lee et al. |
| 5,230,702 A | 7/1993 | Lindsay et al. |
| 5,234,425 A | 8/1993 | Fogarty et al. |
| 5,246,424 A | 9/1993 | Wilk |
| 5,248,298 A | 9/1993 | Bedi et al. |
| 5,250,025 A | 10/1993 | Sosnowski et al. |
| 5,250,033 A | 10/1993 | Evans et al. |
| 5,261,888 A | 11/1993 | Semm |
| 5,275,611 A | 1/1994 | Behl |
| 5,279,554 A | 1/1994 | Turley |
| 5,279,567 A | 1/1994 | Ciaglia et al. |
| 5,312,360 A | 5/1994 | Behl |
| 5,312,417 A | 5/1994 | Wilk |
| 5,316,360 A | 5/1994 | Feikema |
| 5,318,542 A | 6/1994 | Hirsch et al. |
| 5,318,588 A | 6/1994 | Horzewski et al. |
| 5,320,611 A | 6/1994 | Bonutti et al. |
| 5,330,501 A | 7/1994 | Tovey et al. |
| 5,353,785 A | 10/1994 | Wilk |
| D352,018 S | 11/1994 | Robert et al. |
| 5,380,290 A | 1/1995 | Makower et al. |
| 5,392,766 A | 2/1995 | Masterson et al. |
| 5,403,278 A | 4/1995 | Ernst et al. |
| 5,405,334 A | 4/1995 | Roth et al. |
| 5,407,427 A | 4/1995 | Zhu et al. |
| 5,407,430 A | 4/1995 | Peters |
| 5,409,469 A | 4/1995 | Schaerf |
| D358,465 S | 5/1995 | Klein et al. |
| 5,415,178 A | 5/1995 | Hsi et al. |
| 5,431,676 A | 7/1995 | Dubrul et al. |
| 5,433,708 A | 7/1995 | Nichols et al. |
| 5,437,631 A | 8/1995 | Janzen |
| 5,443,484 A | 8/1995 | Kirsch et al. |
| 5,453,094 A | 9/1995 | Metcalf et al. |
| 5,454,790 A | 10/1995 | Dubrul |
| 5,458,579 A | 10/1995 | Chodorow et al. |
| 5,460,170 A | 10/1995 | Hammerslag |
| 5,460,607 A | 10/1995 | Miyata et al. |
| 5,484,403 A | 1/1996 | Yoakum et al. |
| 5,487,739 A | 1/1996 | Aebischer et al. |
| 5,489,279 A | 2/1996 | Meserol |
| 5,496,292 A | 3/1996 | Burnham |
| 5,527,276 A | 6/1996 | Bruce |
| 5,533,986 A | 7/1996 | Mottola et al. |
| 5,540,658 A | 7/1996 | Evans et al. |
| 5,542,928 A | 8/1996 | Evans et al. |
| 5,556,376 A | 9/1996 | Yoon |
| 5,569,200 A | 10/1996 | Umeno et al. |
| 5,573,511 A | 11/1996 | Yoon |
| 5,573,517 A | 11/1996 | Bonutti et al. |
| 5,577,993 A | 11/1996 | Zhu et al. |
| 5,647,859 A | 7/1997 | Lampropoulos et al. |
| 5,647,860 A | 7/1997 | Roth et al. |
| 5,665,076 A | 9/1997 | Roth et al. |
| 5,672,168 A | 9/1997 | de la Torre et al. |
| 5,674,240 A | 10/1997 | Bonutti et al. |
| 5,683,347 A | 11/1997 | Miyata et al. |
| 5,695,462 A | 12/1997 | Sutcu et al. |
| 5,713,867 A | 2/1998 | Morris |
| 5,743,882 A | 4/1998 | Luther |

(56) References Cited

U.S. PATENT DOCUMENTS

| | | |
|---|---|---|
| 5,772,639 A | 6/1998 | Lampropoulos et al. |
| 5,797,886 A | 8/1998 | Roth et al. |
| 5,800,390 A | 9/1998 | Hayakawa et al. |
| 5,800,409 A | 9/1998 | Bruce |
| 5,814,058 A | 9/1998 | Carlson et al. |
| 5,817,062 A | 10/1998 | Flom et al. |
| 5,817,072 A | 10/1998 | Lampropoulos et al. |
| 5,827,319 A | 10/1998 | Carlson et al. |
| 5,836,913 A | 11/1998 | Orth et al. |
| 5,885,217 A | 3/1999 | Gisselberg et al. |
| 5,938,587 A | 8/1999 | Taylor et al. |
| 5,938,645 A | 8/1999 | Gordon |
| 5,957,913 A | 9/1999 | de la Torre et al. |
| 5,961,499 A | 10/1999 | Bonutti et al. |
| 6,004,341 A | 12/1999 | Zhu et al. |
| 6,024,736 A | 2/2000 | de la Torre et al. |
| 6,027,480 A | 2/2000 | Davis et al. |
| 6,030,364 A | 2/2000 | Durgin et al. |
| 6,030,402 A | 2/2000 | Thompson et al. |
| 6,056,766 A | 5/2000 | Thompson et al. |
| 6,077,250 A | 6/2000 | Snow et al. |
| 6,080,174 A | 6/2000 | Dubrul et al. |
| 6,090,072 A | 7/2000 | Kratoska et al. |
| 6,095,967 A | 8/2000 | Black et al. |
| 6,139,532 A | 10/2000 | Howell et al. |
| 6,245,052 B1 | 6/2001 | Orth et al. |
| 6,273,874 B1 | 8/2001 | Parris |
| 6,273,899 B1 | 8/2001 | Kramer |
| 6,287,322 B1 | 9/2001 | Zhu et al. |
| 6,315,770 B1 | 11/2001 | de la Torre et al. |
| 6,319,246 B1 | 11/2001 | de la Torre et al. |
| 6,325,789 B1 | 12/2001 | Janzen et al. |
| 6,325,812 B1 | 12/2001 | Dubrul et al. |
| 6,338,730 B1 | 1/2002 | Bonutti et al. |
| 6,363,273 B1 | 3/2002 | Mastrorio et al. |
| 6,368,337 B1 | 4/2002 | Kieturakis et al. |
| 6,398,799 B2 | 6/2002 | Kramer |
| 6,402,722 B1 | 6/2002 | Snow et al. |
| 6,420,550 B2 | 7/2002 | Elsas, II et al. |
| 6,425,908 B2 | 7/2002 | Ravenscroft et al. |
| 6,428,511 B2 | 8/2002 | Manhes |
| 6,447,527 B1 | 9/2002 | Thompson et al. |
| 6,447,540 B1 | 9/2002 | Fontaine et al. |
| 6,450,989 B2 | 9/2002 | Dubrul et al. |
| 6,463,361 B1 | 10/2002 | Wang et al. |
| 6,464,690 B1 | 10/2002 | Castaneda et al. |
| 6,482,175 B1 | 11/2002 | Walker |
| 6,494,893 B2 | 12/2002 | Dubrul et al. |
| 6,500,170 B2 | 12/2002 | Palmer et al. |
| 6,503,245 B2 | 1/2003 | Palmer et al. |
| 6,524,326 B1 | 2/2003 | Zhu et al. |
| 6,564,078 B1 | 5/2003 | Marino et al. |
| 6,572,624 B2 | 6/2003 | U et al. |
| 6,572,631 B1 | 6/2003 | McCartney |
| 6,579,281 B2 | 6/2003 | Palmer et al. |
| 6,592,573 B2 | 7/2003 | Castaneda et al. |
| D480,140 S | 9/2003 | Harding et al. |
| 6,679,900 B2 | 1/2004 | Kieturakis et al. |
| 6,685,721 B1 | 2/2004 | Kramer |
| 6,692,465 B2 | 2/2004 | Kramer |
| 6,695,856 B2 | 2/2004 | Kieturakis et al. |
| 6,712,795 B1 | 3/2004 | Cohen |
| 6,714,841 B1 | 3/2004 | Wright et al. |
| 6,726,699 B1 | 4/2004 | Wright et al. |
| 6,728,599 B2 | 4/2004 | Wang et al. |
| 6,758,853 B2 | 7/2004 | Kieturakis et al. |
| 6,785,593 B2 | 8/2004 | Wang et al. |
| 6,793,653 B2 | 9/2004 | Sanchez et al. |
| 6,799,088 B2 | 9/2004 | Wang et al. |
| 6,821,287 B1 | 11/2004 | Jang |
| 6,824,554 B1 | 11/2004 | Jang |
| 6,836,703 B2 | 12/2004 | Wang et al. |
| 6,839,612 B2 | 1/2005 | Sanchez et al. |
| 6,840,951 B2 | 1/2005 | de la Torre et al. |
| 6,852,107 B2 | 2/2005 | Wang et al. |
| 6,871,117 B2 | 3/2005 | Wang et al. |
| 6,887,194 B2 | 5/2005 | Hart et al. |
| 6,890,342 B2 | 5/2005 | Zhu et al. |
| 6,892,112 B2 | 5/2005 | Wang et al. |
| 6,951,535 B2 | 10/2005 | Ghodoussi et al. |
| 6,953,467 B2 | 10/2005 | Kieturakis et al. |
| 6,964,675 B2 | 11/2005 | Zhu et al. |
| 6,965,812 B2 | 11/2005 | Wang et al. |
| 7,008,377 B2 | 3/2006 | Beane et al. |
| 7,070,586 B2 | 7/2006 | Hart et al. |
| 7,074,231 B2 | 7/2006 | Jang |
| 7,094,218 B2 | 8/2006 | Rome et al. |
| 7,144,413 B2 | 12/2006 | Wilford et al. |
| 7,179,272 B2 | 2/2007 | Kieturakis et al. |
| 7,189,249 B2 | 3/2007 | Hart et al. |
| 7,214,236 B2 | 5/2007 | Kieturakis et al. |
| 7,217,240 B2 | 5/2007 | Snow |
| 7,229,460 B2 | 6/2007 | Kramer |
| 7,239,940 B2 | 7/2007 | Wang et al. |
| 7,294,136 B2 | 11/2007 | Dubrul et al. |
| 7,297,153 B2 | 11/2007 | Kieturakis et al. |
| 7,300,448 B2 | 11/2007 | Criscuolo et al. |
| 7,309,328 B2 | 12/2007 | Kaplan et al. |
| 7,408,439 B2 | 8/2008 | Wang et al. |
| 7,413,565 B2 | 8/2008 | Wang et al. |
| 7,422,571 B2 | 9/2008 | Schweikert et al. |
| 7,449,011 B2 | 11/2008 | Wenchell et al. |
| 7,608,082 B2 | 10/2009 | Cuevas et al. |
| 8,795,326 B2 | 8/2014 | Richard |
| 2002/0035373 A1 | 3/2002 | Carlson et al. |
| 2003/0100909 A1 | 5/2003 | Suzuki |
| 2005/0197537 A1* | 9/2005 | Bonadio ............ A61B 17/0293 600/208 |
| 2006/0162672 A1 | 7/2006 | Dokken |
| 2008/0188897 A1 | 8/2008 | Krebs et al. |

FOREIGN PATENT DOCUMENTS

| | | |
|---|---|---|
| DE | 4020956 A1 | 1/1991 |
| DE | 91025532 | 7/1991 |
| DE | 91065534 | 9/1991 |
| EP | 0177177 A2 | 4/1986 |
| EP | 0385920 A2 | 9/1990 |
| EP | 0391396 A2 | 10/1990 |
| EP | 0487175 A1 | 5/1992 |
| EP | 1523948 A1 | 4/2005 |
| EP | 1702575 A2 | 9/2006 |
| FR | 748666 A | 7/1933 |
| FR | 2439591 A1 | 5/1980 |
| GB | 2154608 A | 9/1985 |
| GB | 2199247 A | 7/1988 |
| JP | 5743726 | 3/1982 |
| JP | 57197901 | 12/1982 |
| JP | 08019550 | 1/1996 |
| SU | 1331495 A1 | 8/1987 |
| SU | 1528465 A1 | 12/1989 |
| WO | 8904638 A1 | 6/1989 |
| WO | 9219312 A1 | 11/1992 |
| WO | 9221294 A1 | 12/1992 |
| WO | 9530374 A1 | 11/1995 |
| WO | 9819730 A1 | 5/1998 |
| WO | 9829026 A2 | 7/1998 |
| WO | 9906094 A1 | 2/1999 |
| WO | 9917665 A1 | 4/1999 |
| WO | 03011154 A2 | 2/2003 |
| WO | 2004047654 A2 | 6/2004 |
| WO | 2005003233 A1 | 1/2005 |

OTHER PUBLICATIONS

Japanese Office Action 2008-259099 dated Jan. 23, 2013.

\* cited by examiner

FIG. 7

EXPANDING SEAL ANCHOR FOR SINGLE INCISION SURGERY

CROSS-REFERENCE TO RELATED APPLICATIONS

This application is a continuation of U.S. patent application Ser. No. 12/244,127 filed Oct. 2, 2008, now U.S. Pat. No. 8,795,326, which claims benefit of U.S. Provisional Application No. 60/997,844 filed Oct. 5, 2007, and the disclosures of each of the above-identified applications are hereby incorporated by reference in their entirety.

BACKGROUND

1. Technical Field

The present disclosure relates to a device, and a method of use thereof, for facilitating access to a patient's internal cavities during a surgical procedure. More particularly, the present disclosure relates to a surgical anchoring apparatus adapted for insertion into an incision in tissue, and for the sealed reception of one or more surgical objects, so as to form a substantially fluid-tight seal with both the tissue and the surgical object, or objects.

2. Background of the Related Art

Today, many surgical procedures are performed through small incisions in the skin, as compared to the larger incisions typically required in traditional procedures, in an effort to reduce trauma to the patient and recovery time. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures. During a typical minimally invasive procedure, surgical objects, such as surgical access devices, e.g. trocar and cannula assemblies, or endoscopes, are inserted into the patient's body through the incision in tissue.

In generally, prior to the introduction of the surgical object into the patient's body, insufflation gasses are used to enlarge the area surrounding the target surgical site to create a larger, more accessible work area. Accordingly, the maintenance of a substantially fluid-tight seal at the incision and about the surgical object, or objects, is desirable so as to prevent the escape of the insufflation gases and the deflation or collapse of the enlarged surgical work area.

To this end, various apparatus, including valves, seals and the like, are used during the course of minimally invasive procedures and are widely known in the art. However, a continuing need exists for a self-anchoring apparatus that can be inserted directly into the incision in tissue and that can accommodate a variety of surgical objects while maintaining the integrity of an insufflated workspace.

SUMMARY

In one aspect of the present disclosure, a surgical anchoring apparatus includes a body member defining a longitudinal body passage extending along a longitudinal axis thereof, a dilator element at least partially positionable within the longitudinal passage of the body member and a seal mounted with respect to the dilator element.

The body member includes an expandable section adapted to transition between a first initial condition and a second expanded condition. The expandable section of the body member includes a plurality of expandable segments separated by slots, which may be substantially longitudinal, and a plurality of internal cam surfaces that are obliquely arranged with respect to the longitudinal axis defined by the body member. In one embodiment, each of the expandable segments includes an internal cam surface. The expandable section further includes an outer helical thread adapted to facilitate the advancement of the body member within tissue when the body member is in the first initial condition.

The body member also includes a grip segment adapted for manual engagement by a user. The grip segment depends radially outwardly relative to the longitudinal axis of the body member. The grip segment is adapted to transition between a normal state and an at least partially inverted state. The grip segment may comprise an elastomeric material, and have a peripheral flange that is adapted to contact tissue when the grip segment is in the normal state. The peripheral flange may be adapted to establish a vacuum seal with the tissue upon transition of the grip segment from the at least partially inverted state to the normal state.

The dilator element is dimensioned to cause the expandable section to transition to the second expanded condition when inserted into the expandable section to thereby facilitate securement of the body member relative to tissue. The dilator element defines a longitudinal dilator passage for the reception and passage of a surgical object. The dilator element is dimensioned to contact the cam surfaces during insertion of the dilator element within the longitudinal passage of the body member to move the expandable segments at least radially outwardly relative to the longitudinal axis and cause the transition of the expandable section to the second expanded condition.

The seal is adapted to establish a substantial sealing relation with the surgical object received within the dilator element. In alternate embodiments, the seal may include a gel material or a self healing foam material.

These and other features of the valve disclosed herein will become more readily apparent to those skilled in the art from the following detailed description of various embodiments of the present disclosure.

BRIEF DESCRIPTION OF THE DRAWINGS

Various embodiments of the present disclosure are described hereinbelow with references to the drawings, wherein.

DETAILED DESCRIPTION OF THE EMBODIMENTS

In the drawings and in the description which follows, in which like reference numerals identify similar or identical elements, the term "proximal" will refer to the end of the apparatus which is closest to the clinician during the use thereof, while the term "distal" will refer to the end which is furthest from the clinician, as is traditional and known in the art.

Figure 1:
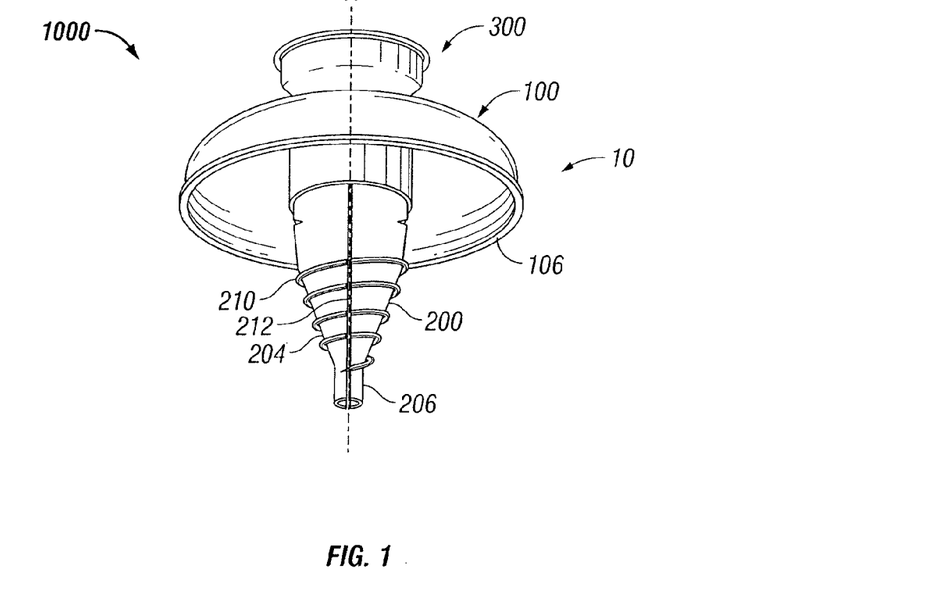
FIG. 1 is a side perspective view of a surgical anchoring apparatus in accordance with the principles of the present disclosure illustrating a body member and a dilator element.
Figure 2:
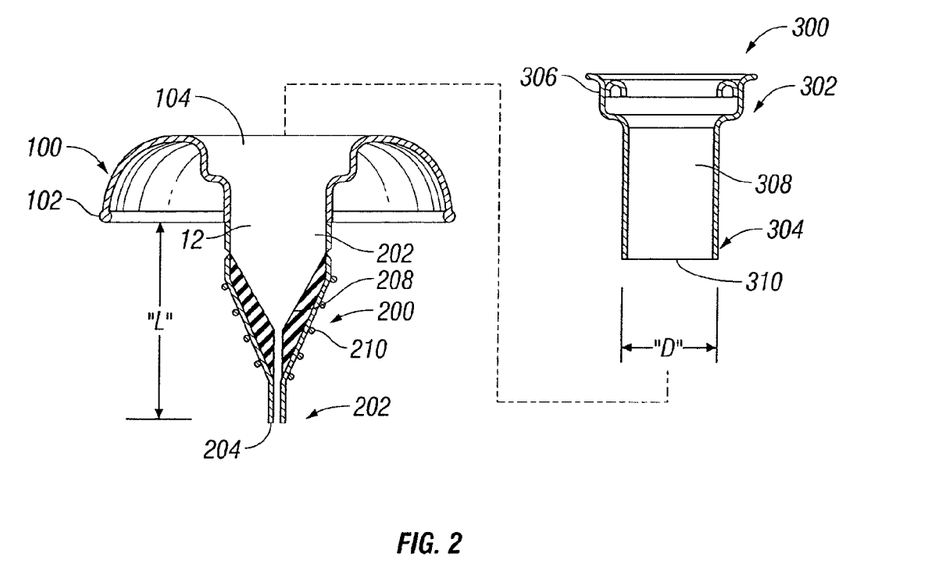
FIG. 2 is a side cross-sectional view of the surgical anchoring apparatus of FIG. 1 with the dilator element removed from the body member.
Figure 3:
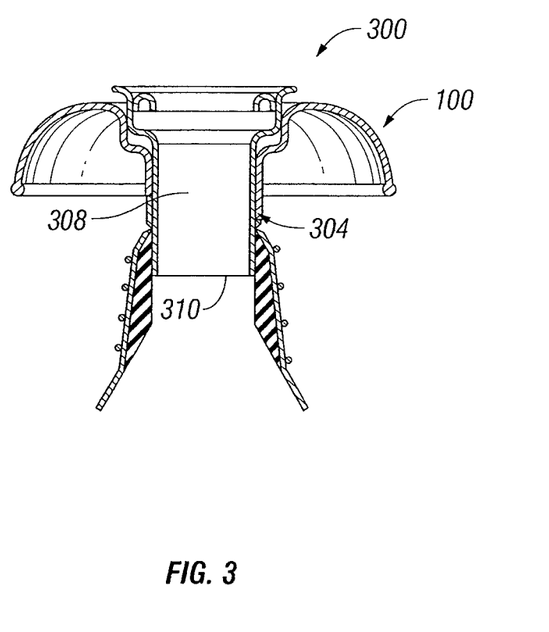
FIG. 3 is a side cross-sectional view of the surgical anchoring apparatus of FIG. 2 with the dilator element inserted in the body member.

With reference now to FIGS. 1-2, a surgical anchoring apparatus 1000 is disclosed for use in a surgical procedure, e.g. a minimally invasive procedure. Anchoring apparatus 1000 includes a body member 10 and a dilator element 300 at least partially positionable therein. Body member 10 defines a longitudinal axis "A" and a longitudinally extending passage 12 and includes a grip segment 100 and an expandable section 200.

Figure 6:
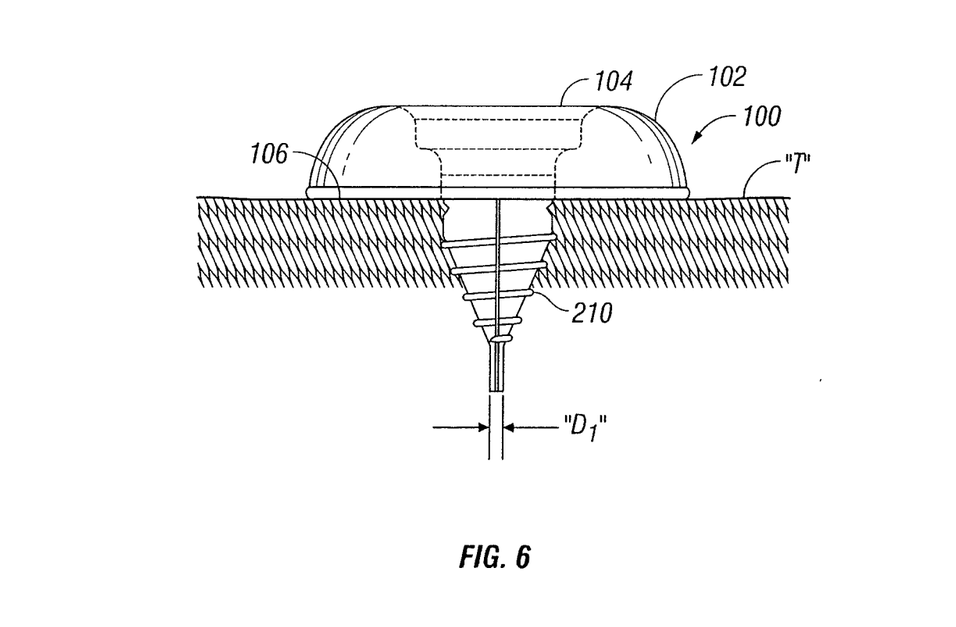
FIG. 6 is a side plan view of the body member of the surgical anchoring apparatus illustrating the grip segment in a second normal state.

Grip segment 100 depends radially outward relative to the longitudinal axis "A" of body member 10 and includes an outer surface 102 having an aperture 104 formed therein that is dimensioned to receive dilator element 300. Outer surface 102 extends outwardly from aperture 104 to a peripheral flange 106. Peripheral flange 106 is adapted to contact and establish a substantially vacuum quality seal with tissue "T" (see FIGS. 6-7), as discussed below.

Figure 4:
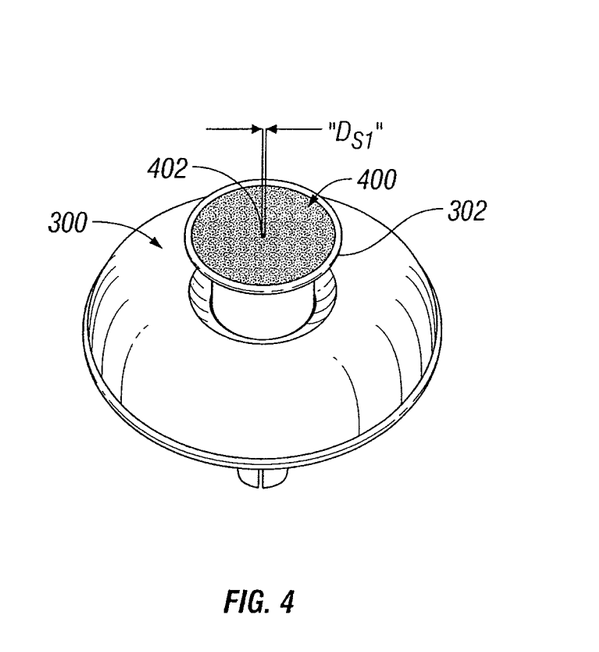
FIG. 4 is a top perspective view of the surgical anchoring apparatus of FIG. 1 illustrating details of the seal.
Figure 5:
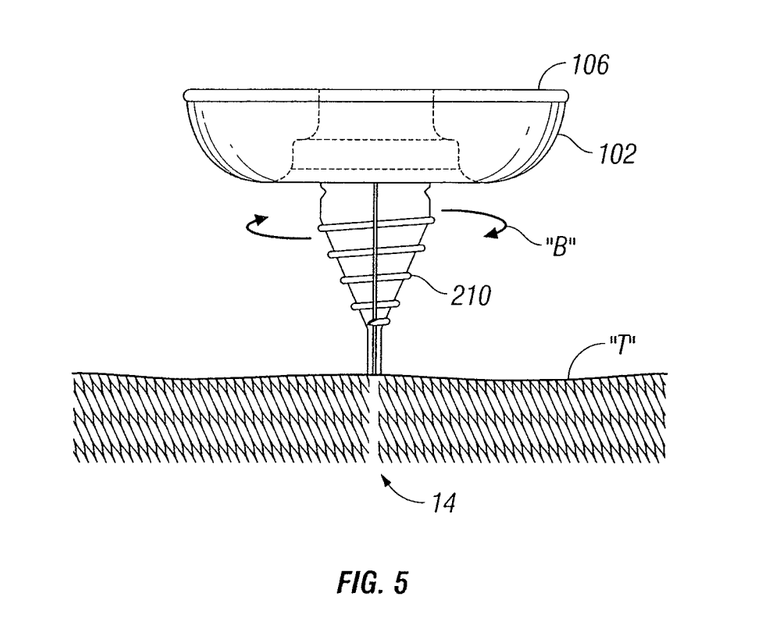
FIG. 5 is a side plan view of the body member of the surgical anchoring apparatus illustrating the grip segment in a first inverted state.

Grip segment 100 is adapted for manual engagement by a user and to resiliently transition between a first or normal state (FIGS. 1-4) and a second state (FIG. 5). In the first state, outer surface 102 of grip segment 100 exhibits a substantially distal curvature in which peripheral flange 106 is directed distally. In the second state, grip segment 100 is at least partially inverted such that at least a portion of outer surface 102 exhibits a substantially proximal curvature such that peripheral flange 106 is directed proximally. In this state, grip segment 100 is more aptly configured for manual engagement by a user to facilitate the insertion of expandable section 200 into an incision 14 (FIG. 5), as discussed in further detail below. It should be noted that engagement by a user is also possible when grip segment 100 is in the first state. Grip segment 100 may be formed of any suitable biocompatible material that is sufficiently flexible to permit grip segment 100 to resiliently transition between the first and second states, including but not being limited to elastomeric materials.

Figure 7:
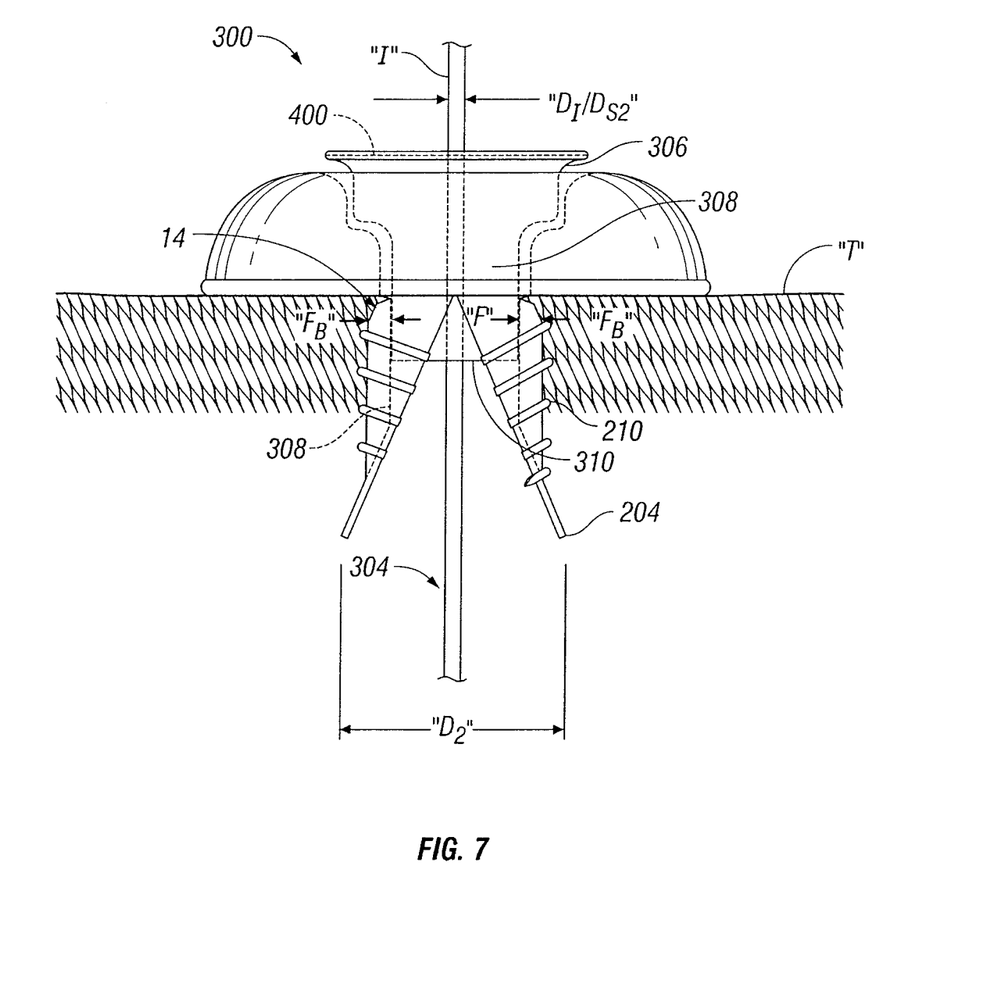
FIG. 7 is a side plan view of the surgical anchoring apparatus illustrating the dilator element inserted through the body member, and an expandable section of the body member in a second, expanded condition.

Expandable section 200 extends distally from grip segment 100 and is in substantial alignment with aperture 104 of grip segment 100 such that dilator element 300 may pass through aperture 104 and into expandable section 200 upon insertion. At its distal end 202, expandable section 200 defines an opening 204 that is dimensioned to allow a distal end 304 of dilator element 300 to pass therethrough. Expandable section 200 is adapted to transition from a first, or initial condition (FIG. 6) to a second, or expanded condition (FIG. 7).

Expandable section 200 defines a length "L" that is sufficient to provide percutaneous access to a patient's underlying cavities, organs and the like (not shown). Expandable section 200 includes a plurality of expandable segments 206, a plurality of internal cam surfaces 208 and an outer helical thread 210.

Expandable segments 206 are defined by two or more slots 212. In one embodiment, slots 212 extend in a substantially longitudinal manner. However, alternate configurations for slots 212 are not beyond the scope of the present disclosure. Upon the transition of expandable section 200 from the initial condition to the expanded condition, expandable segments 206 are splayed radially outward, as discussed in further detail below.

Internal cam surfaces 208 are obliquely arranged with respect to the longitudinal axis "A" defined by body member 10. Internal cam surfaces 208 are configured to engage a tapered outer surface 308 of dilator element 300 upon its insertion into longitudinal passage 12 of body member 10 to facilitate the transition of expandable section 200 from the initial condition to the expanded condition, as discussed in further detail below. In one embodiment, each expandable segment 206 includes an internal cam surface 208. Outer helical thread 210 is disposed on the outer surface of expandable section 200. Helical thread engages tissue "T" upon the insertion of expandable section 200 into incision 14 so as to facilitate the distal advancement of body member 10. In addition, helical thread 210 may assist in the anchoring of body member 10 within tissue "T".

Expandable section 200 may be formed of any suitable biocompatible material that is sufficiently resilient to permit resilient expandable section 200 to resiliently transition between the initial and expanded conditions thereof.

In its first, or normal condition, expandable section 200 is configured for insertion into incision 14 and defines a first diameter "$D_1$". Upon the insertion of dilator element 300, a distal end 304 thereof engages cam surfaces 208. As dilator element 300 is advanced distally through longitudinal passage 12, its distal end 304 forces cam surfaces 208, and expandable segments 206, outwardly to thereby transition expandable section 200 into its expanded condition. In its expanded condition, expandable section 200 defines a second, larger diameter "$D_2$".

Dilator element 300 has a proximal end 302 that includes a seal 400 and a gripping portion 306 that is configured for grasping by a user during the distal advancement of dilator element 300 through body member 10.

Dilator element 300 defines a longitudinal passage 308 that extends therethrough from its proximal end 302 to its distal end 304 where an opening 310 is defined. Longitudinal passage 308 defines a diameter "D" and is configured to removably receive one or more surgical objects "I" (FIG. 7), e.g. a trocar, endoscope or surgical stapler. The diameter "D" of longitudinal passage 308 may range between about 3 mm to about 15 mm, or may be substantially within the range of about 5 mm to about 12 mm. However, the use of surgical objects having substantially larger and smaller diameters is contemplated herein, as is a dilator element 300 defining a longitudinal passage 308 with a substantially larger or smaller diameter "D" so as to accommodate such surgical objects. In one embodiment, the longitudinal dilator passage 308 is divided into a plurality of individual lumens (not shown) separated by at least one septum. Each of the individual lumens may be of either substantially similar or substantially different dimensions and are each configured to receive a surgical object.

Dilator element 300 may be formed of any biocompatible material that is sufficiently rigid to urge the expandable segments 206 of expandable section 200 outwardly upon its insertion into longitudinal body passage 12 and thereby transition expandable portion 200 from its normal condition to its expanded condition.

Referring now to FIGS. 4 and 7, seal 400 is associated with proximal end 302 of dilator element 300 and may be mounted thereto. Seal 400 defines an aperture 402 and is adapted to transition from a closed condition (FIG. 4) to an open condition (FIG. 7) upon the insertion of surgical object "I". In the closed condition, aperture 402 defines a first dimension "$D_{S1}$" of about 0 mm so as to substantially prevent the escape of any insufflation gas (not shown) therethrough in the absence of surgical object "I". Upon the insertion of surgical object "I", aperture 402 is forced open, thereby transitioning seal 400 into the open condition. In this condition, aperture 402 defines a second dimension "$D_{S2}$" that substantially approximates the diameter "$D_I$" of surgical object "I" such that seal 400 forms a substantially fluid-tight seal with surgical object "I", thereby substantially preventing the escape of any insufflation gas through seal 400. Surgical object "I" will generally define a diameter substantially within the range of about 5 mm to about 12 mm. Accordingly, in the second condition, aperture 402 will generally define a second dimension "$D_{S2}$" that is also substantially within the range of about 5 mm to about 12 mm. However, the use of surgical objects having substantially larger and smaller diameters is contemplated herein, as is a seal 400 with an aperture 402 that is capable of accommodating such surgical objects.

Seal 400 may be formed of any suitable biocompatible material that is at least semi-resilient in nature such that seal 400 may transition between the closed and open conditions thereof. Seal 400 may be any seal or valve suitable for the intended purpose of removably receiving a surgical object in sealed relation therewith, including but not being limited to a slit-valve or a zero closure valve.

The use and function of anchoring apparatus 1000 during the course of a minimally invasive procedure will now be discussed. Initially, the peritoneal cavity (not shown) is insufflated with a suitable biocompatible gas such as, e.g., $CO_2$ gas, such that the cavity wall is raised and lifted away from the internal organs and tissue housed therein, providing greater access thereto. The insufflation may be performed with an insufflation needle or similar device, as is conventional in the art. Either prior or subsequent to insufflation, an incision 14 is created in tissue "T", the dimensions of which may be varied dependent upon the nature of the surgical procedure.

Prior to the insertion of anchoring apparatus 1000 within incision 14, dilator element 300 is removed from body 10. Thereafter, the clinician may transition grip segment 100 from the first state (FIGS. 1-4) to the second state (FIG. 5) to facilitate the manual engagement thereof and the insertion of body member 10. To realize this transition, the user at least partially inverts grip segment 100 such that the outer surface 102 exhibits a proximal curvature. Once in the second state, the clinician may more easily grasp grip segment 100, e.g. about peripheral flange 106.

The distal end 206 of expandable section 200 is then inserted into and advanced distally through incision 14. Optionally, the clinician may rotate body 10, e.g. clockwise in the direction of arrows "B", during insertion such that helical thread 210 facilitates the distal advancement of expandable section 200. After expandable section 200 has been completely inserted within the patient's tissue "T", grip segment 100 is returned to its first state such that peripheral flange 106 is in engagement with tissue "T". Grip segment 100 may form a substantially vacuum seal with tissue "T". (See FIGS. 6-7).

Subsequently, dilator element 300 is inserted through aperture 104 in grip segment 100, into longitudinal body passage 202, distally therethrough and into expandable section 200. During the distal advancement of dilator element 300, its distal end 304 engages cam surfaces 208, thereby forcing the plurality of expandable segments 206 outwardly and transitioning expandable section 200 from the normal condition (FIG. 6) to the expanded condition (FIG. 7). As previously discussed, in the normal condition, expandable section 200 defines a first diameter "$D_1$" and in the expanded condition, expandable section 200 defines a second, larger diameter "$D_2$".

During the transition from the first condition to the second condition, expandable section 200 expands outwardly and exerts a force "F" upon tissue "T" which dilates incision 14. Force "F" creates a corresponding biasing force "$F_B$" within tissue "T" that attempts to close incision 14. Forces "F" and "$F_B$" collaborate to secure and anchor expandable section 200 within tissue "T" in a substantially fluid tight manner such that the escape of insufflation gas about anchoring apparatus 1000 is substantially prevented. In addition, while inserted within tissue "T", helical thread 210 is disposed distally, and perhaps proximally, of tissue "T", thereby further securing the disposition and anchoring of expandable section 200 within tissue "T".

Finally, surgical object "I" is inserted and advanced distally through the seal 400 associated with the proximal end 302 of dilator element 300, through longitudinal dilator passage 308 and ultimately through opening 310 at the distal end 304 of dilator element 300. Thereafter, the remainder of the surgical procedure may be carried out using surgical object "I".

Upon completion of the surgical procedure, surgical object "I" is withdrawn from dilator element 300 through seal 400. Dilator element 300 is then withdrawn from expandable section 200 through longitudinal body passage 202 and through aperture 104 in grip segment 100. During the withdrawal of dilator element 300, force "F" dissipates, as does the corresponding biasing force "$F_B$" in tissue "T", thereby facilitating the withdrawal of expandable section 200. The user may then transition grip segment 100 from the first state to the second state and withdraw body member 10 from incision 14, optionally rotating body member 10 during withdrawal. Incision 14 may then be closed.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical apparatus, comprising:
    a body dimensioned for at least partial insertion through tissue and defining a longitudinal body passage, the body including:
        a grip segment having an outer surface, the grip segment being adapted to transition between a first state where the outer surface is distally directed and a second state where the outer surface is proximally directed; and
        an elongate segment extending from the grip segment, the elongate segment adapted to transition between a first condition defining a first internal dimension and a second condition defining a second internal dimension different than the first internal dimension; and
    a dilator at least partially positionable within the longitudinal body passage of the body, and being dimensioned to cause the elongate segment to transition to the second condition.

2. The surgical apparatus according to claim 1 wherein the dilator defines a longitudinal dilator passage for passage of an object.

3. The surgical apparatus according to claim 2 wherein the dilator includes a seal.

4. The surgical apparatus according to claim 1 wherein the elongate segment includes at least one expandable member, the at least one expandable member adapted to be displaced radially outwardly relative to a longitudinal axis of the elongate segment during insertion of the dilator within the longitudinal body passage of the body.

5. The surgical apparatus according to claim 4 wherein the at least one expandable member includes at least one internal cam surface, the at least one internal cam surface configured to cooperate with the dilator to displace the at least one expandable member radially outwardly during insertion of the dilator within the longitudinal body passage of the body.

6. The surgical apparatus according to claim 1 wherein the grip segment includes a peripheral flange.

7. The surgical apparatus according to claim 6 wherein the peripheral flange is dimensioned and adapted to establish a seal with tissue upon transition of the grip segment to the second state.

8. The surgical apparatus according to claim 1 wherein at least a portion of the outer surface has a distal curvature when the grip segment is in the first state and has a proximal curvature when the grip segment is in the second state.

9. A surgical method, comprising:
providing the surgical apparatus of claim 1;
positioning the grip segment in the second state;
grasping the grip segment and advancing the body within tissue to provide access to an underlying surgical site;
transitioning the grip segment from the second state to the first state; and
engaging at least a peripheral segment of the outer surface of the grip segment when in the first state thereof with tissue.

10. The method according to claim 9 further including expanding the elongate segment from the first condition defining the first internal dimension to the second condition defining the second internal dimension different than the first internal dimension.

11. The method according to claim 10 wherein expanding the elongate segment includes introducing the dilator at least partially into the elongate segment of the body.

12. The method according to claim 11 further including performing a surgical procedure by introducing a surgical object through a dilator passage of the dilator.

13. The method according to claim 9 wherein engaging the at least a peripheral segment of the outer surface of the grip segment includes establishing a seal with the peripheral segment of the outer surface of the grip segment with the tissue.

14. The method according to claim 9 wherein positioning the grip segment includes arranging the grip segment such that at least a portion of the outer surface curves proximally and wherein transitioning the grip segment from the second state to the first state includes arranging the grip segment such that the at least a portion of the outer surface curves distally.

15. The method according to claim 9 further including performing a surgical procedure through the longitudinal body passage of the body.

16. The method according to claim 15 wherein performing the surgical procedure includes introducing a surgical object through the longitudinal body passage of the body.

* * * * *